United States Patent
Grodzins et al.

[19]

[11] Patent Number: 6,151,381
[45] Date of Patent: Nov. 21, 2000

[54] GATED TRANSMISSION AND SCATTER DETECTION FOR X-RAY IMAGING

[75] Inventors: Lee Grodzins, Lexington; Roderick D. Swift, Belmont, both of Mass.

[73] Assignee: American Science and Engineering, Inc., Billerica, Mass.

[21] Appl. No.: 09/238,686

[22] Filed: Jan. 27, 1999

Related U.S. Application Data

[60] Provisional application No. 60/072,890, Jan. 28, 1998, and provisional application No. 60/089,714, Jun. 18, 1998.

[51] Int. Cl.$^7$ .................................................... G01N 23/04
[52] U.S. Cl. ............................................. 378/90; 378/57
[58] Field of Search ................................. 378/51, 53, 54, 378/57, 62, 70, 86, 87, 88, 89, 90

[56] References Cited

U.S. PATENT DOCUMENTS

| | | | |
|---|---|---|---|
| 4,047,029 | 9/1977 | Allport ........................................ | 378/90 |
| 4,864,142 | 9/1989 | Gomberg ............................ | 250/390.04 |
| 4,884,289 | 11/1989 | Glockmann et al. ...................... | 378/57 |
| 5,065,418 | 11/1991 | Bermbach et al. ........................ | 378/57 |
| 5,313,511 | 5/1994 | Annis et al. ............................... | 378/87 |
| 5,428,657 | 6/1995 | Papanicoloploulos et al. ........... | 378/86 |
| 5,600,303 | 2/1997 | Husseiny et al. ........................ | 340/568 |
| 5,600,700 | 2/1997 | Krug et al. ................................ | 378/57 |
| 5,642,393 | 6/1997 | Krug et al. ................................ | 378/57 |
| 5,692,029 | 11/1997 | Husseiny et al. .......................... | 378/88 |
| 5,940,468 | 8/1999 | Huang et al. ............................. | 378/57 |
| 5,974,111 | 10/1999 | Krug et al. ................................ | 378/57 |

*Primary Examiner*—David P. Porta
*Attorney, Agent, or Firm*—Bromberg & Sunstein LLP

[57] ABSTRACT

An inspection system for inspecting an enclosure and its contents using temporally gated sources of penetrating radiation. A first source produces an intermittent first beam having a duration of inactivity while a second sources produces a second beam, which may have an energy spectrum differing from that of the first beam, during the inactivity of the first beam. One detector generates a transmission signal based on penetrating radiation transmitted through the enclosure while a scatter detector generates a scatter signal based on penetrating radiation scattered by the contents of the enclosure. The scatter detector may be gated for non-detection during the pulsing of the transmission beam. A processor derives properties of the contents of the enclosure on the basis of the transmission signal and the scatter signal.

18 Claims, 8 Drawing Sheets

GATED TRANSMISSION AND SCATTER DETECTION FOR X-RAY IMAGING

This application claims priority from U.S. Provisional Application Ser. No. 60/072,890, filed Jan. 28, 1998, and from U.S. Provisional Application Ser. No. 60/089,714, filed Jun. 18, 1998, which applications are herein incorporated by reference.

TECHNICAL FIELD

The present invention relates to an x-ray system and method for concurrently imaging an object in higher-energy photons transmitted through the object and in lower-energy photons scattered by the object.

BACKGROUND OF THE INVENTION

X-rays are often used for the inspection of enclosures such as cargo containers. The use of x-rays both transmitted through the inspected item and scattered by its contents are known in the art. Typically, the item is illuminated by a single source of x-rays, and transmitted and scattered radiation is detected by detectors or arrays of detectors disposed, respectively, in the direction of propagation of the illuminating beam or in other directions, to the front, back, or sides of the inspected item.

To obtain useful images of the x-rays transmitted through heavily loaded containers, such as truck trailers or sea shipping containers, etc., often 6 feet to 10 feet thick, it is necessary to use x-rays with energies well in excess of 1 MeV. Lower energy x-rays may be attenuated to the point that they can no longer be detected by detectors on the side of the container opposite to the side illuminated by the x-ray source. Typical commercial x-ray systems such as those employed for the purposes described above use linear accelerators to generate x-rays from electrons having energies from 5 MeV to 10 MeV; the average energy of the x-ray spectrum generated by a 10 MeV machine is approximately 3 MeV.

Images obtained from transmitted x-rays, however, are insensitive to thin, light material. Scattered radiation, in particular backscattered radiation may be used to obtain images of such thin objects not too far inside the containers and also to discriminate organic from non-organic objects. Various methods of identifying a backscatter signal with a position within the illuminated object employ scanned pencil beams of x-rays, are described, for example, in U.S. Pat. Nos. 4,809,312 and 4,825,454 which are hereby incorporated herein by reference.

At lower x-ray energies, i.e. <~450 keV, it is practical to obtain a transmission image and a backscatter image simultaneously using the x-rays from a single x-ray generator. As the energy of the x-rays increases, however, the method of backscatter imaging becomes less and less practical for three reasons: First, the probability of scattering into the back directions (i.e. through about 180°) drops rapidly as the energy of the x-rays increase. Thus MeV x-ray beams produce relatively weak backscatter signals. Second, the backscatter signal becomes independent of the scattering material for x-ray energies above a few hundred keV. Thus, backscattering from beams having energies in the MeV range, such as those discussed in connection with transmission imaging of large containers, provide insufficient material discrimination. Third, while backscatter imaging typically employs a "pencil" beam of x-rays to raster across the container, such that the cross sectional dimensions of the beam determine the spatial resolution of the backscatter image, it is technically difficult to form a scanning pencil beam of MeV x-rays.

SUMMARY OF THE INVENTION

In accordance with one aspect of the invention, in one of its embodiments, there is provided an inspection system for inspecting an enclosure and its contents. The system has a first source for producing an intermittent first beam of penetrating radiation having a duration of inactivity and at least one detector for generating a transmission signal based on at least the penetrating radiation transmitted through the enclosure. Additionally, the system has a second source for producing a second beam of penetrating radiation and at least one detector for generating a scatter signal based on at least the penetrating radiation scattered by the contents of the enclosure. The system also has a processor for deriving properties of the contents of the enclosure on the basis of the transmission signal and the scatter signal.

In accordance with an embodiment of the invention, the first and second beams may have different energy spectra. In particular, the first beam may be a high-energy beam. The at least one detector for generating a transmission signal may be gated for detection substantially only during the pulsing of the high-energy transmission beam. The scatter detector may be gated for non-detection during the pulsing of the transmission beam.

In accordance with another embodiment of the invention, the system may also have a steerable electron beam for generating the first and second beams of penetrating radiation.

BRIEF DESCRIPTION OF THE DRAWINGS

The foregoing features of the invention will be more readily understood by reference to the following detailed description taken with the accompanying drawings in which.

DETAILED DESCRIPTION OF PREFERRED EMBODIMENTS

In accordance with preferred embodiments of the invention, both a high energy transmission image and a low-energy backscatter image may be obtained of the same object or container during a single pass of the container through an inspection system. Dual transmission and backscatter imaging may be achieved by using a single accelerator as a source of x-rays, such as by changing the electron energy, temporally alternating between peak energies of 5 MeV and 450 keV. This, however, is not a useful solution since it may be desirable to use entirely different beam shapes for the transmission and backscatter modalities. In particular, a fan beam may be effective for producing the transmission image and may be inexpensively generated by a pulsed accelerator. On the other hand, a pencil beam, most readily formed by a continuous wave accelerator, may be preferable for backscatter imaging since pencil beam irradiation allows the spatial source of scattered radiation to be readily identified.

Figure 1:
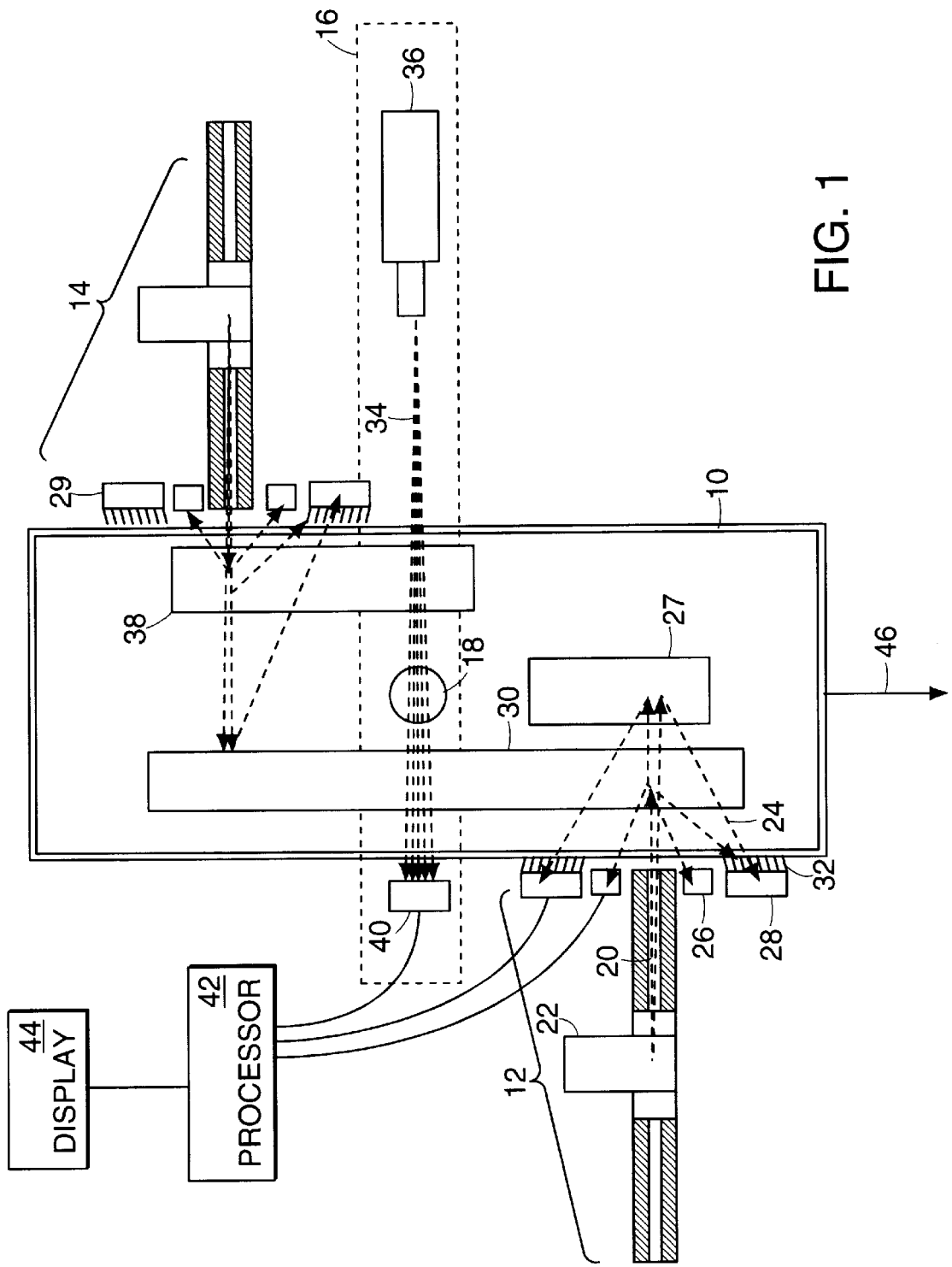
FIG. 1 is a schematic top view of an x-ray inspection configuration employing independent transmission and backscatter systems in accordance with an embodiment of the present invention.

In accordance with embodiments of the present invention, independent x-ray generators are used to provide sources of penetrating radiation for transmission and scatter images. One or more x-ray generators may be used for each modality. Referring to FIG. 1, a top view of a cargo container 10 being examined by two backscatter x-rays systems 12 and 14, one on either side of container 10, and two orthogonal transmission systems, one horizontal 16, the other vertical 18.

Describing, first, backscatter x-rays systems 12 and 14, x-ray beam 20 is emitted by an x-ray source 22 of one of various sorts known to persons skilled in the art. Beam 20 may also be comprised of other forms of penetrating radiation and may be monoenergetic or multi-energetic, or, additionally, of varying spectral characteristics. Backscatter x-ray beam 20 is typically generated by a DC voltage applied to the anode of an x-ray tube 22 so that beam 20 is typically continuous. However, a beam 20 of other temporal characteristics is within the scope of the invention. Beam 20 has a prescribed cross sectional profile, typically that of a flying spot or pencil beam. Beam 20 will be referred to in the present description, without limitation, as an x-ray beam, and also, without limitation, as a pencil beam. In a preferred embodiment of the invention, a scanned pencil beam, whose position and cross section is well known at every point in time, is used. The cross section of the pencil beam defines the spatial resolution of the images. Typical pencil beam sizes are a few mm in diameter at a distance of a meter from the beam defining collimation; that is, an angular spread in the beam of <5 milliradians.

Backscatter beam 20 is typically characterized by x-ray energies in the range below 300 keV, so that detected backscatter has a component significantly dependent on the composition of the scattering material. Penetrating radiation scattered by an object 27 within enclosure 10 is detected by one or more x-ray detectors 26 and 28. X-ray detectors 28 disposed more distantly from x-ray beam 20 than other detectors 26 detect x-rays singly scattered only from more distant objects 27 whereas any scattering incident on outer detector 28 from a near-field object 30 must be due to multiple scattering of the x-ray radiation within the near-field object and is thereby sharply attenuated. Consequently, inner detectors 26 are preferentially more sensitive to near-field objects 30, while outer detectors 28 are preferentially more sensitive to far-field objects 27. Since beam 20 is typically a pencil beam, i.e., a beam having a narrow angular extent, typically on the order of 1°, the source of detected scattering may be localized both with respect to depth and with respect to lateral position. In order to obtain greater spatial resolution of the source of scattered radiation, collimators 32 may be employed, as known to persons skilled in the x-ray art, for narrowing the field of view of segments of detector 28.

Transmission systems 16 and 18 are now described. X-ray beam 34 is produced by source 36 which is typically a high energy source of penetrating radiation such as a linear accelerator (Linac) for example. In a preferred embodiment of the invention, beam 34 is a fan beam, subtending typically 30°. The transmission x-ray source from a linear accelerator is inherently pulsed, with typical pulse rates in the range between 100 and 400 pulses per second. The x-ray intensity used for transmission, namely the total x-ray power emitted at source 36, is several orders of magnitude greater than that of x-ray beam 20 used for scattering, mainly because the latter is a pencil beam subtending <<1°, while the former is a fan beam subtending about 30°, so that comparable detector signal-to-noise in a background limited environment requires substantially larger transmission beam fluxes. The portion of transmission beam 34 which traverses enclosure 10 and objects 30 and 38 contained within the enclosure is detected by transmission detector 40.

The electrical output signals produced by detectors 26, 28, and 40 are processed by processor 42 to derive characteristics such as the geometry, position, density, mass, and effective atomic number of the contents from the scatter signals and transmission signals using algorithms known to persons skilled in the art of x-ray inspection. In particular, images of the contents of enclosure 10 may be produced by an image generator. As used in this description and in the appended claims, the term "image" refers to an ordered representation of detector signals corresponding to spatial positions. For example, the image may be an array of values within an electronic memory, or, alternatively, a visual image may be formed on a display device 44 such as a video screen or printer. The use of algorithms, as known in the art of x-ray inspection, for identifying suspect regions within the enclosure, and identification of the presence of a specified condition by means of an alarm or otherwise, is within the scope of the present invention.

In many applications, it is desirable that enclosure 10 be inspected in a single pass of the enclosure through the x-ray inspection system. Enclosure 10 may move through the system in a direction indicated by arrow 46, either by means of self-propulsion or by any means of mechanical conveyance, such as conveyor 49 (shown in FIG. 2) of the enclosure with respect to the system. It is to be understood that motion of the system with respect to the enclosure is an equivalent application of the invention.

One problem that must be overcome, if one or more transmission images and one or more scatter images are to be obtained in a single pass of the enclosure through the x-ray inspection system, is that of the elimination of cross talk between the transmission and scatter systems. In particular, radiation from the intense transmission beam 34 may scatter from material within enclosure 10 and be detected by backscatter detectors 26 and 28 that must count relatively low rates and are thus very sensitive even to highly attenuated and multiply scattered radiation originating within transmission beam 34.

In accordance with a preferred embodiment of the present invention, the backscatter signals and transmission signals are rendered completely independent of one another by temporal gating of the different detectors, as described in greater detail below.

Figure 2:
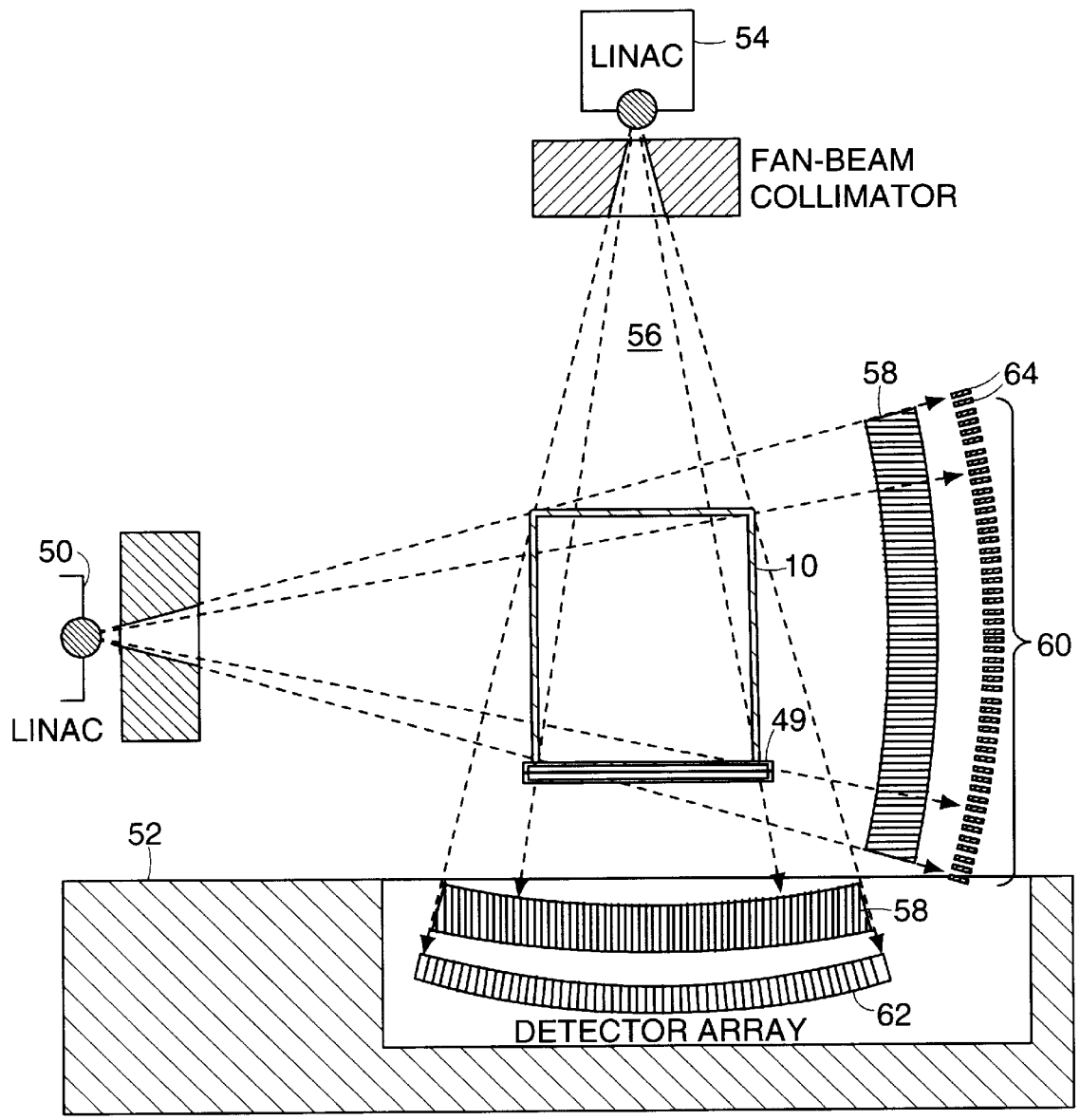
FIG. 2 is a schematic elevation view in cross section of the transmission imaging components of the inspection system of FIG. 1.

Referring now to FIG. 2, a schematic is shown of a side view in cross section of transmission imaging systems 16 and 18 of the inspection system of FIG. 1. A first linear accelerator 50 is horizontal, i.e., parallel to the ground 52. A second linear accelerator 54 shines its x-rays 56 into the ground. Collimators 58 are placed in front of each Linac to produce narrow fan beams of x-rays that pass through the container into arrays 60 and 62 of detectors. The cross section of individual detectors 64 in the direction of the x-ray beam determines the spatial resolution of the transmitted image.

Figure 3:
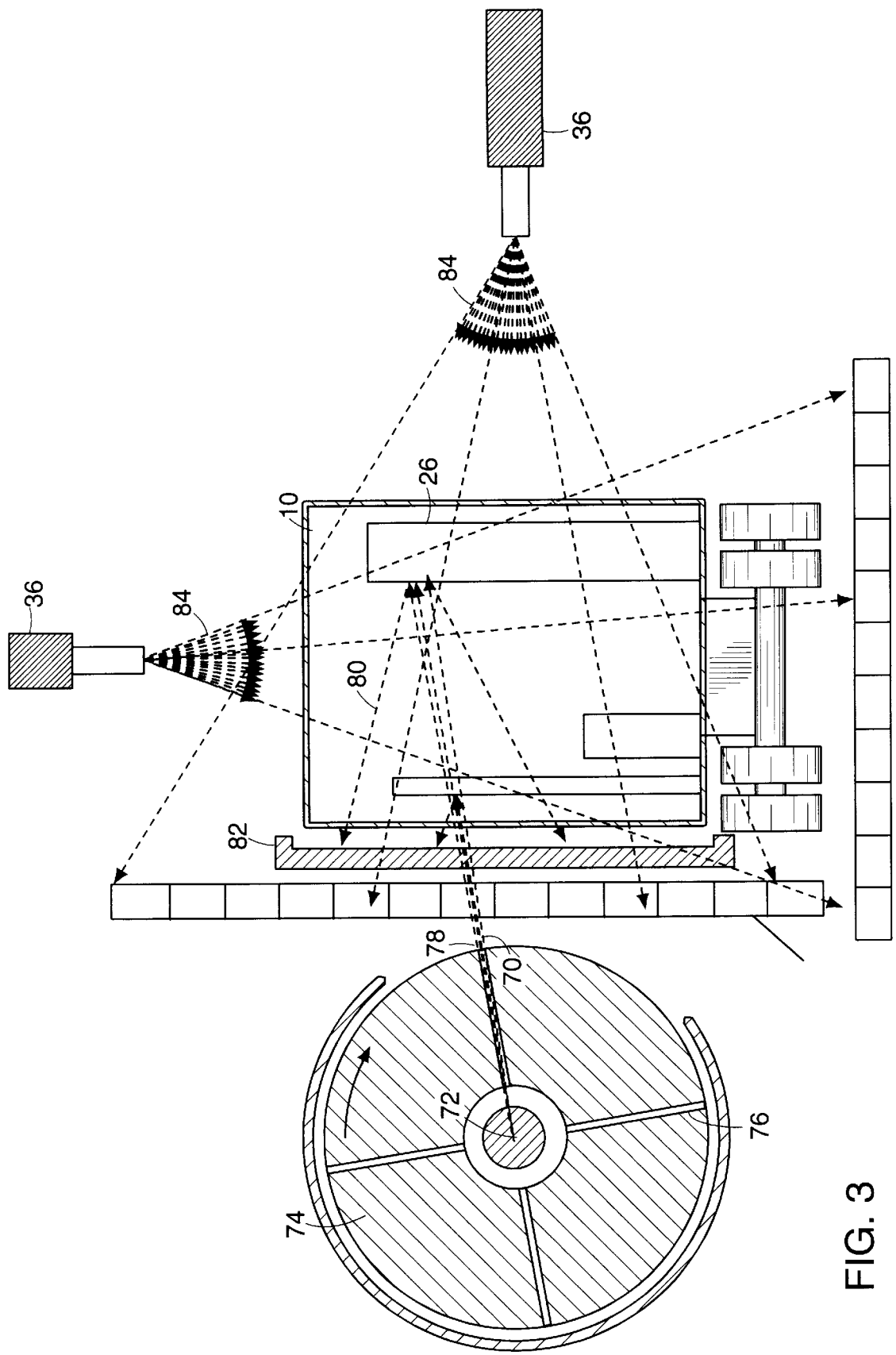
FIG. 3 is an elevation schematic of an inspection system in accordance with a preferred embodiment of the invention, showing one of the scanning pencil beam systems used for backscatter imaging.

FIG. 3 is a schematic of an elevation view of an inspection system in accordance with a preferred embodiment of the invention. Only one backscattered x-ray system is shown, although two or more backscatter systems may be present, as designated by numerals 12 and 14 in FIG. 1. X-ray beam 70, generated by an x-ray source 72 in the center of a rotating wheel 74, pass out of the wheel 74 through hollow spokes 76. Rotating wheel 74 is an x-ray blocking material such as lead. The beam size is determined by exit hole 78 at the end of the spokes 76. As wheel 74 turns, x-ray beam 70 sweeps across container 10. Various scanning mechanisms are known to persons skilled in the art to provide for scanning of beam 70 across a region of space which may include the target container 10, all such scanning mechanisms being within the scope of the present invention. X-rays 80 backscattered from objects 26 within container 10 are detected in long backscatter detectors 82 on either side of x-ray beam 10. Transmission beams 84 are sketched in for reference.

Figure 4:
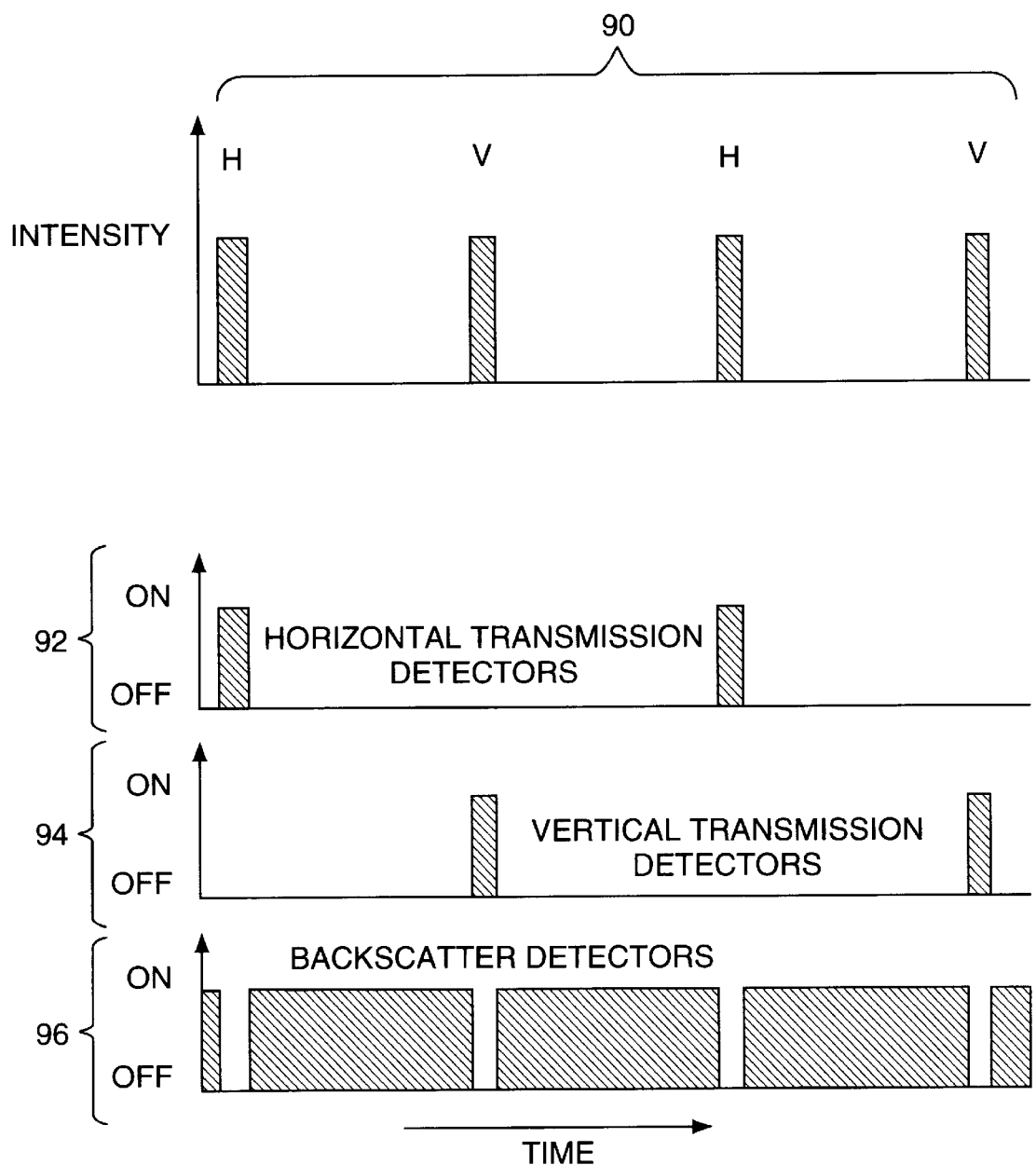
FIG. 4 shows a sequence for gating the transmission and backscatter detectors in accordance with the embodiment of FIG. 1.

Referring now to FIG. 4, a sequence is shown for gating the Linacs and the transmission and backscatter detectors in accordance with a preferred embodiment of the invention. The upper part of the figure shows the pulse sequence 90 from two linear accelerators as a function of time plotted on the horizontal axis, with H representing pulsing of the horizontal Linac and V representing pulsing of the vertical Linac. Typically, the pulse width is 5 $\mu$s, repeated every 5 ms; i.e. 200 pulses per second. The vertical and horizontal accelerators are synchronized so that the x-ray beams alternate every 2.5 ms.

The lower part of FIG. 4 shows the "on-time" structure of the detectors which are easily gated on and off with microsecond timing. The time line for the vertical detectors is shown in line 92, that for the horizontal transmission detectors in line 94 and that for the backscatter detectors in line 96. The horizontal and vertical x-ray detectors are gated on only during the times when the respective x-rays are on. In this way each of the detectors in insensitive to any radiation or detector noise that is present when their respective x-ray beams are off. The timing introduces no loss of signal for the transmission detectors and only an 0.2% loss of signal for the backscatter detectors which are off for 5 $\mu$s every 2.5 ms.

Referring again to FIG. 1, the only cross talk between the detectors is between the two backscatter detectors 28 and 29. That cross talk is minimized by spatially separating the backscatter systems 12 and 14. A 15 feet separation, which is quite practical when scanning a 40-foot container, reduces the cross talk to insignificance since pencil beams 70 are relatively weak. The placement of Linacs 36 and 18 is a matter of design choice, and the Linacs may be placed, for example, in an intermediate position between the backscatter detectors, as shown in FIG. 1.

Figure 5:
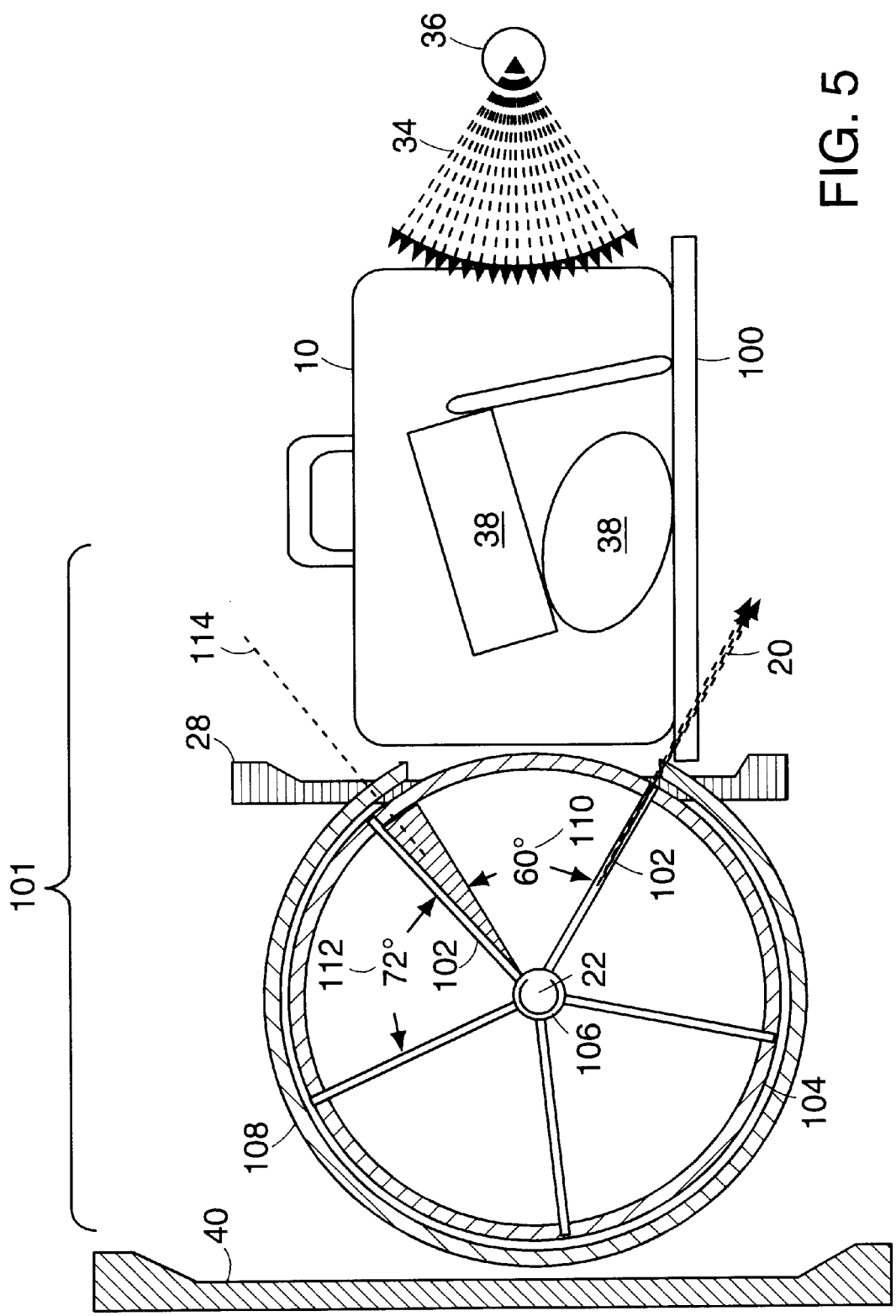
FIG. 5 is a schematic view in cross section of an x-ray inspection configuration employing a source of a fan beam for transmission measurements and a source of a scanning pencil beam for scattering measurements, in accordance with an alternate embodiment of the present invention.

The use of alternately gated transmission and scattering functionalities in accordance with the present invention is not limited to the embodiments heretofore described. Referring now to FIG. 5, a further embodiment of the invention is shown schematically from the side, wherein two independent x-ray generating systems illuminate an inspected object 10 in temporal sequence. Object 10, shown as a suitcase containing articles 38. Suitcase 10 may be inspected while being conveyed in a direction out of the drawing by means of conveyor 100. A transmission inspection system consists of x-ray generator 36 that emits a fan beam 34 of x-rays. Transmitted x-rays from beam 34 traverse object 10 and are detected by transmission detector 40, which may comprise an array of individual detectors. A separate backscatter system consists of a second x-ray generator 22 and a mechanism, designated generally by numeral 101, for causing x-ray beam 20 to scan object 10. Beam 34 used for transmission detection and beam 20 used for scatter detection may be oriented in any way with respect to one another within the scope of the invention. They may, for example, be on opposite sides of object 10 as shown, or may be on the same side, or on adjacent sides.

One possible embodiment of scanning mechanism 101 as depicted in FIG. 5, causes x-ray beam 20 to pass out of hollow spokes 102 of rotating wheel 104, in the manner of a swept pencil beam. As wheel 104 rotates, x-ray beam 20 sweeps out of the spokes in the manner of water from a sprinkler hose. An inner collimator 106 and an outer collimator 108 restrict the emerging x-rays to an arc 110 of the order of 60°. Hollow spokes 102 in the embodiment shown have a spacing 112 of 72°, so that, as wheel 104 turns, there are periods (represented by sector 114) during which beam 20 is not incident upon object 10. During these "dead" spaces, backscatter detectors 28 may be inactivated and fan beam 34 turned on.

Figure 6:
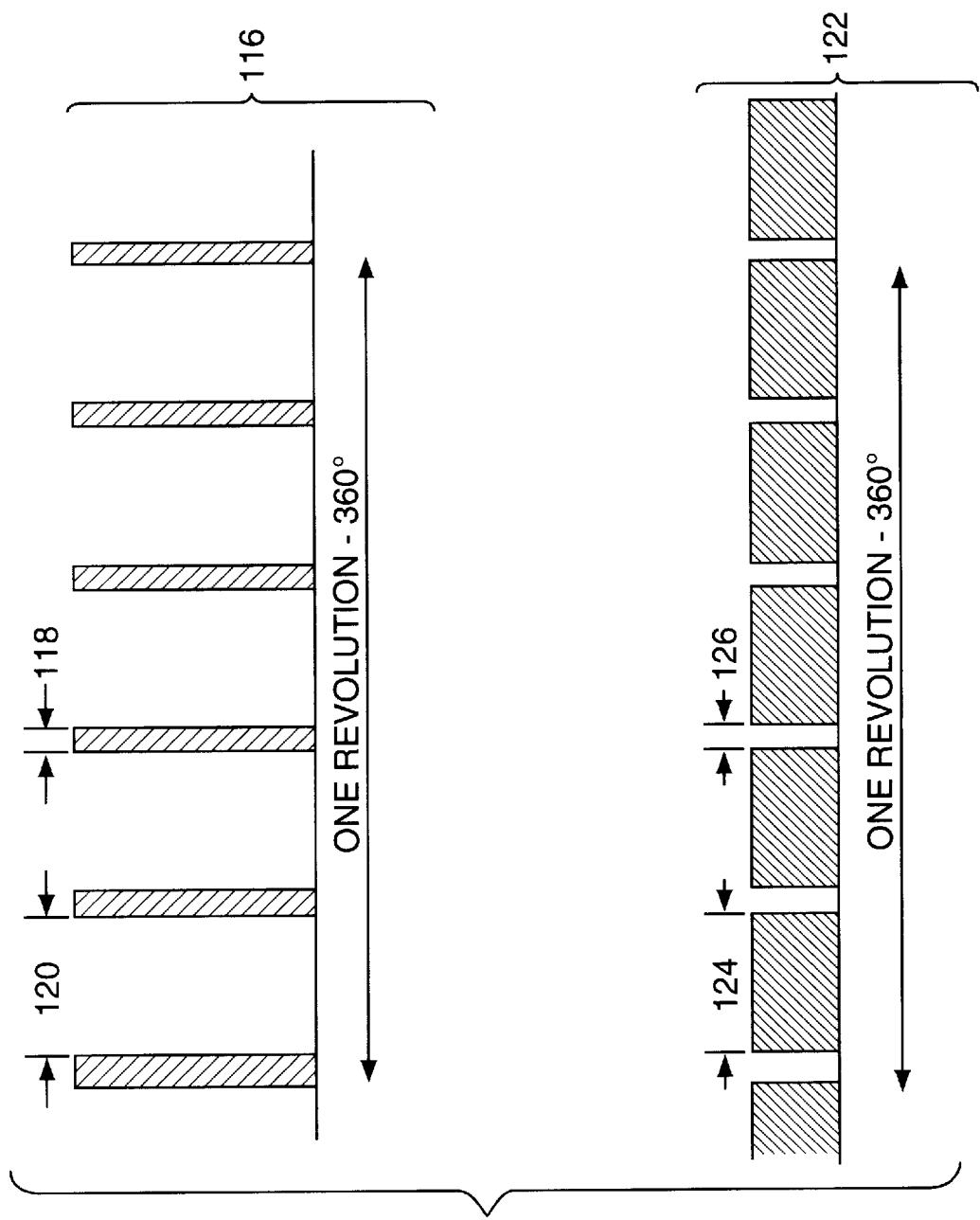
FIG. 6 shows a sequence for gating the transmission and backscatter detectors in accordance with the embodiment of FIG. 5.

A timing sequence corresponding to application of the embodiment of FIG. 5 is discussed with reference to FIG. 6. Upper panel 116 depicts the timing of the transmission beam, which, in the embodiment described above is a fan beam. The horizontal axis corresponds to time, calibrated in terms of the rotation of wheel 104. The hatched periods 118 correspond to periods during which transmission beam in on, each period corresponding, in turn, to approximately 11° of rotation of wheel 104. During intervening periods 120, corresponding to approximately 61° of rotation of wheel 104, the transmission beam is inactive. Lower panel 122 depicts the timing of the scatter beam which is substantially complementary to that of the transmission beam. The scatter pencil beam is turned on during periods 124 when the transmission beam is off, and, conversely, the scatter beam is turned off or is otherwise not incident on inspected object 10 during periods 126 when the transmission beam is on. Periods 124 correspond to approximately 60° of rotation of wheel 104, while the off periods for the scatter beam correspond to approximately 12° of rotation. Since the transmission and scatter sources are independent and complementary in timing, the beams may operate at different energies, currents, filtration and focal spot size.

Figure 7:
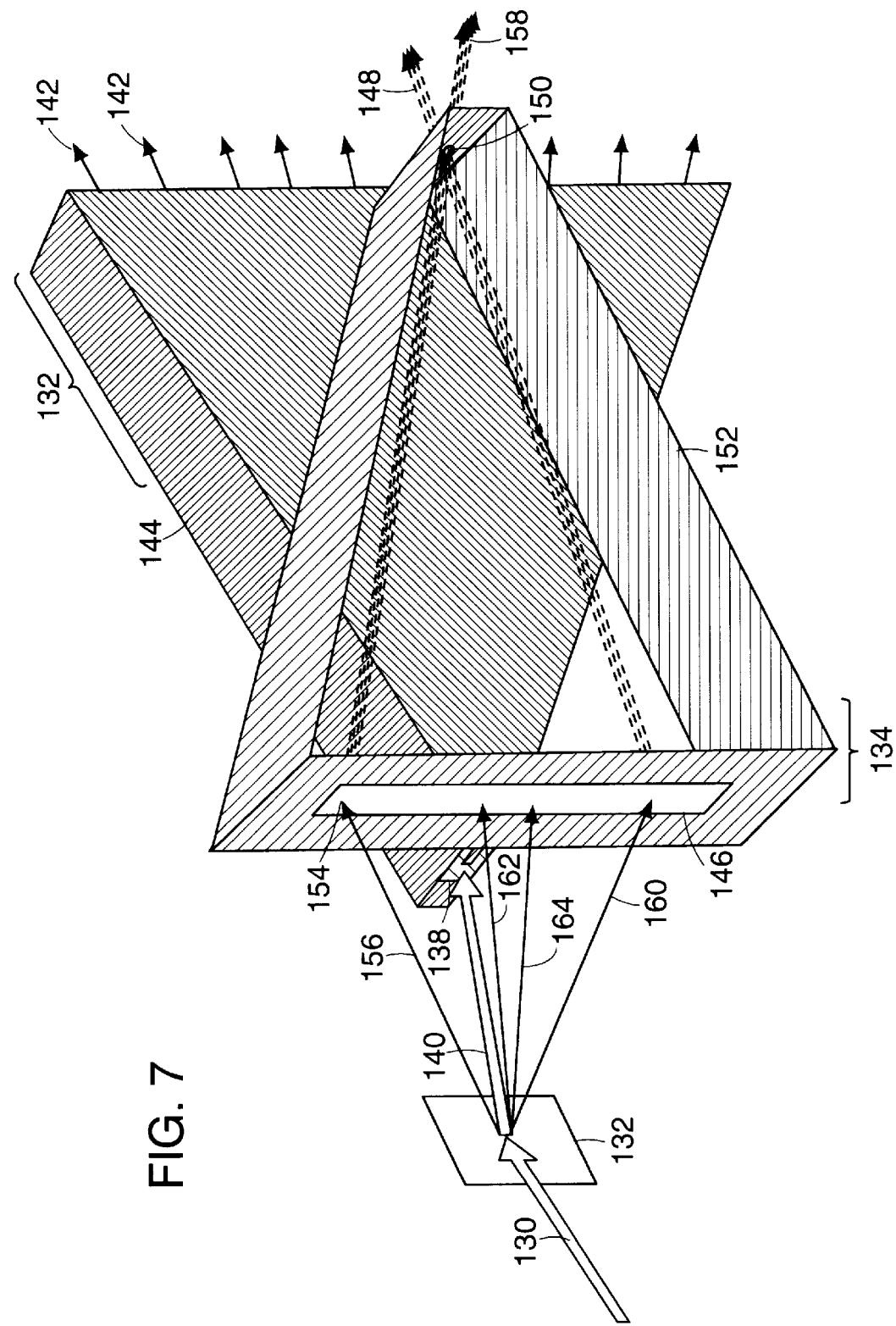
FIG. 7 is a schematic view of an apparatus for generating multiple independent x-ray beams with a single steerable source of electrons, in accordance with an alternate embodiment of the invention.

In accordance with other embodiments of the invention, a single source of electrons may be used to form more than one x-ray beam incident upon an inspected object. Electrons are readily controlled electromagnetically, as known in the art of electron beam tubes generally, and the electrons may be focused and directed to specific locations on anodes where x-rays may be generated. Referring now to FIG. 7, a single electron beam 130 is directed by magnetic or electrostatic deflectors 132, as well known in the art, alternately into a fan beam generator 134 and into a scanning beam generator 136. Any sequence of alternation is within the scope of the invention. One example of a possible sequence is now described. Electron beam 130 may be directed to an anode 138 along path 140 for a specified duration of time. X-rays 142 generated at anode 138 are formed into a fan beam by a collimator 144. At the end of the preset dwell time, electron beam 130 is moved over to long anode 146 over which it is swept upward and/or downward, generating an x-ray beam such as beam 148 that emerges from aperture 150 in collimator 152. Four electron positions 154 are shown on anode 146. Electron beam 156 striking near the top of anode 146 generates an x-ray beam 158 that is directed substantially downward through the inspected container. Electron beam 160 which strikes near the bottom of anode 146 generates x-ray beam 148 that is directed upward through the inspected container. As electron beam 130 sweeps from position 156 through positions 162, 164, to 160, the emergent x-ray beam sweeps through the inspected container. After each cyclical sweep of the x-ray beam, electron beam 130 is directed back to anode 138 to generate a fan beam 142.

The dwell time at anode 138 and the speed and number of sweeps of electron beam 130 across anode 146 can all be varied to optimize the effectiveness of the inspection under particular circumstances.

Figure 8:
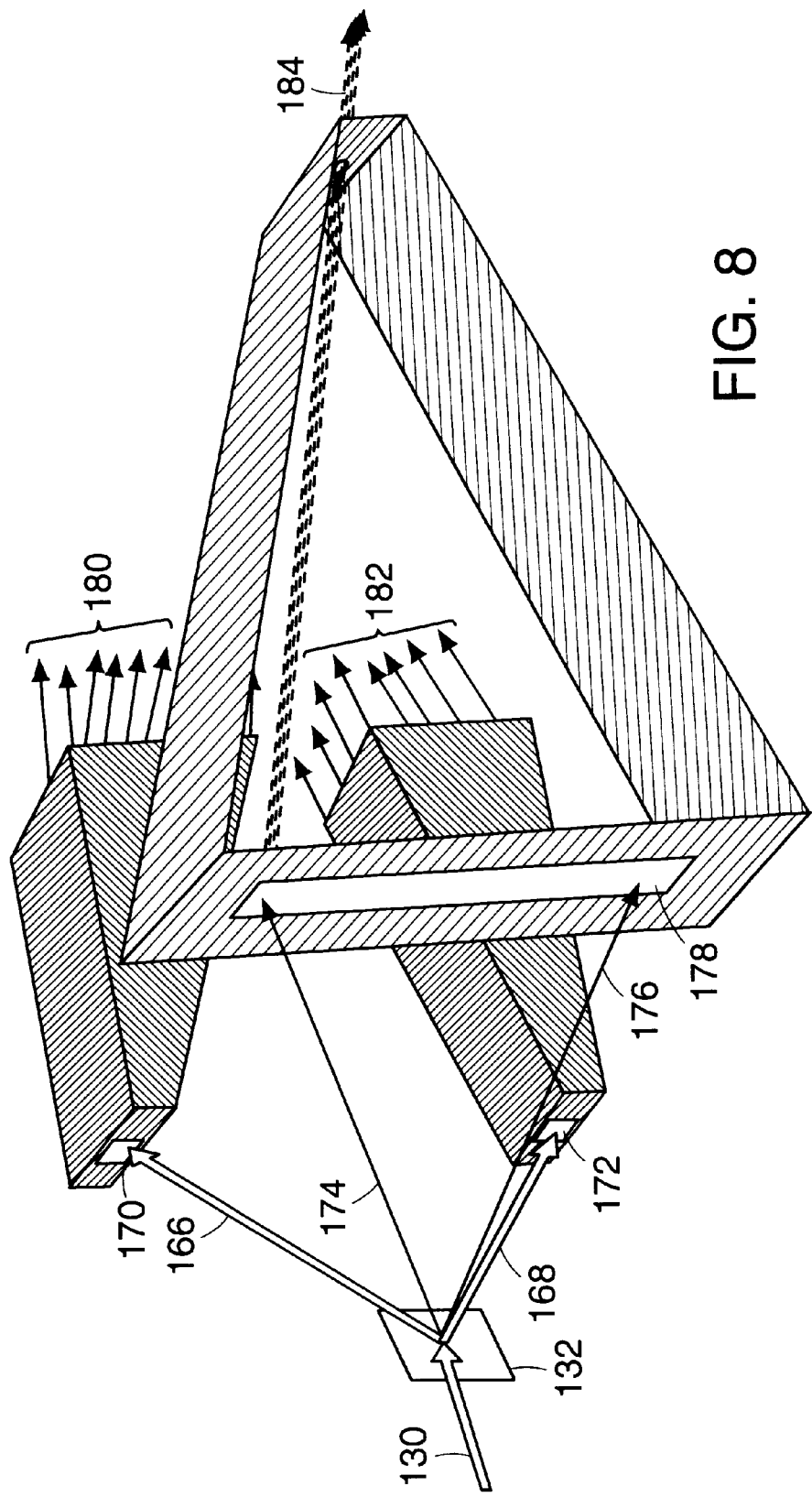
FIG. 8 is a schematic view of a further apparatus for generating multiple independent x-ray beams with a single steerable source of electrons, in accordance with an alternate embodiment of the invention.

Additionally, in accordance with further embodiments of the invention, a steerable source of x-rays may also be employed to obtain images, in transmission and scattering, for dual (or multiple) energy and/or stereoscopic imaging. A further embodiment is shown in FIG. 8, where electron beam 130 is directed by magnetic or electrostatic deflectors 132 in directions 166 and 168 to anodes 170 and 172 respectively, and in directions 174 and 176 to positions along a long anode 178. Alternatively, electron beam 130 may be scanned across anode 178 in two dimensions, creating a pencil beam steerable across the face of the inspected article. In the embodiment shown, electron beam 132 creates two fan beams, 180 and 182, for the production of two stereoscopic images of x-rays transmitted through the inspected container, and, additionally, a scanning pencil beam 184.

It is to be understood that the energy of the electrons in the beam, or, alternatively, their flux, may be varied in any way, during the course of the inspection, within the scope of the invention. Additionally, the relative scanning and dwell times are matters of system design preference. For example, electron beam 130 may first dwell at position 168, then raster across anode 178 to produce a scanning x-ray beam for scatter imaging, then swell on position 166 for the other view of the stereoscopic image, then raster scan across anode 178 again before starting the cycle over, as the inspected container is conveyed through the x-ray beams. It is preferred that the speed of the conveyor being scanned be such that there are no gaps in either the transmission or scatter images.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. An inspection system for inspecting an enclosure having contents, the system comprising:

a. a first source for producing an intermittent first beam of penetrating radiation having a duration of inactivity, b. at least one detector for generating a transmission signal based on at least the penetrating radiation transmitted through the enclosure;

c. a second source for producing a second beam of penetrating radiation, d. at least one detector for generating a scatter signal based on at least the penetrating radiation scattered by the contents of the enclosure during the duration of inactivity of the first source; and e. a processor for deriving properties of the contents of the enclosure on the basis of the transmission signal and the scatter signal.

2. An inspection system according to claim 1, wherein the first source is a linear accelerator.

3. An inspection system according to claim 1, wherein the intermittent first beam is a fan beam.

4. An inspection system according to claim 1, wherein the second beam is a pencil beam.

5. An inspection system according to claim 1, wherein the first source has a first energy spectrum and the second source has a second energy spectrum different from the first energy spectrum.

6. An inspection system according to claim 4, wherein the energy spectrum of the first beam includes x-rays exceeding 1 MeV and the energy spectrum of the second beam includes only x-rays below 500 keV.

7. An inspection system according to claim 1, wherein the processor includes a calculating device for deriving at least one of the density, mass, atomic number, shape, and position of an object disposed within the enclosure.

8. An inspection system according to claim 1, wherein the processor includes an image generator for producing transmission and scatter images.

9. An inspection system according to claim 8, further including a display device for exhibiting at least one of the transmission and scatter images.

10. An inspection system according to claim 1, wherein the first beam is periodically pulsed.

11. An inspection system according to claim 10, wherein the at least one detector for generating a transmission signal is gated for detection substantially only during the pulsing of the first beam.

12. An inspection system according to claim 10, wherein the at least one detector for generating a scatter signal is gated for non-detection during the pulsing of the first beam.

13. An inspection system according to claim 1, further including a steerable electron beam for generating the first beam and the second beam of penetrating radiation.

14. An inspection system according to claim 1, wherein the first beam of penetrating radiation may impinge upon the enclosure from a plurality of directions.

15. A method for inspecting an enclosure, the method comprising:

a. periodically illuminating the enclosure with a pulsed beam of penetrating radiation, b. generating a transmission signal based on at least the penetrating radiation transmitted through the enclosure;

c. scanning the enclosure with a continuous beam of penetrating radiation, d. generating a scatter signal based on at least the penetrating radiation scattered by the contents of the enclosure; and e. deriving properties of the contents of the enclosure on the basis of the transmission signal and the scatter signal.

16. A method according to claim 12, wherein the step of deriving properties of the contents of the enclosure includes deriving at least one of the density, mass, atomic number, shape, and position of an object disposed within the enclosure.

17. A method according to claim 12, wherein the step of generating a scatter signal includes gating the generation of a scatter signal in such a manner that no signal is generated during the periodic illumination of the enclosure with the pulsed beam of penetrating radiation.

18. A method for inspecting an enclosure, the method comprising:
   a. periodically illuminating the enclosure with a first intermittent beam of penetrating radiation having a duration of inactivity;
   b. generating a transmission signal based on at least the penetrating radiation transmitted through the enclosure;
   c. scanning the enclosure with a second beam of penetrating radiation,
   d. generating a scatter signal based on at least the penetrating radiation scattered by the contents of the enclosure during the duration of inactivity of the first intermittent beam; and
   e. deriving properties of the contents of the enclosure on the basis of the transmission signal and the scatter signal.

* * * * *